United States Patent [19]
Macaluso, Sr. et al.

[11] 3,984,486
[45] *Oct. 5, 1976

[54] SYNTHESIS OF LINEAR PRIMARY ALCOHOLS FROM INTERNAL OLEFINS

[75] Inventors: Anthony Macaluso, Sr., Port Arthur; Orville W. Rigdon, Groves, both of Tex.

[73] Assignee: Texaco Inc., New York, N.Y.

[ * ] Notice: The portion of the term of this patent subsequent to Sept. 23, 1992, has been disclaimed.

[22] Filed: June 20, 1975

[21] Appl. No.: 588,930

Related U.S. Application Data

[63] Continuation-in-part of Ser. No. 322,055, Jan. 8, 1973, Pat. No. 3,907,909.

[52] U.S. Cl. .................... 260/632 HF; 260/683.2
[51] Int. Cl.$^2$ .................................... C07C 29/16
[58] Field of Search ............................ 260/632 HF

[56] References Cited
UNITED STATES PATENTS

| | | | |
|---|---|---|---|
| 3,139,460 | 6/1964 | Eisenmann | 260/683.2 |
| 3,239,569 | 3/1966 | Slaugh et al. | 260/632 HF |
| 3,432,570 | 3/1969 | Hoffman et al. | 260/683.2 |
| 3,542,896 | 11/1970 | Butte | 260/683.2 |
| 3,907,909 | 9/1975 | Macaluso et al. | 260/632 HF |

*Primary Examiner*—Joseph E. Evans
*Attorney, Agent, or Firm*—Thomas H. Whaley; Carl G. Ries; Henry W. Archer

[57] ABSTRACT

It has been discovered that heating $C_4$–$C_{17}$ internal olefins to 300°F to 500°F for about 15 to 30 minutes in the presence of an oxo catalyst prior to hydroformylation results in a higher selectivity to primary alcohols than does the conventional hydroformylation procedure of heating all the reactants together.

7 Claims, No Drawings

SYNTHESIS OF LINEAR PRIMARY ALCOHOLS FROM INTERNAL OLEFINS

CROSS-REFERENCE TO CO-PENDING APPLICATION

This application is a continuation-in-part of coassigned patent application Ser. No. 322,055 filed Jan. 8, 1873, and now issued as U.S. Pat. No. 3,907,909.

BACKGROUND OF THE INVENTION

This invention is concerned with the preparation of linear primary alcohols from predominantly internal olefins.

The oxo or hydroformylation reaction is an important commercial method for the preparation of aldehydes and/or alcohols from olefins which may be shown in the general case by the following equation:

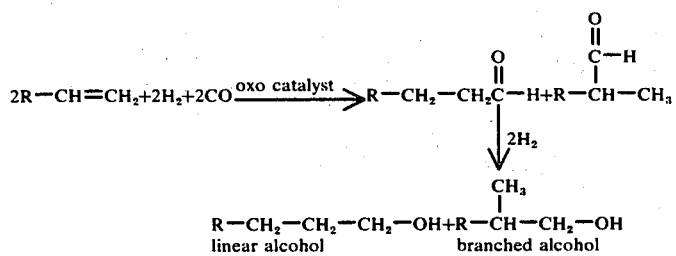

Alcohols produced by the above reaction or "oxo" alcohols find use as solvents, intermediates in platicizer manufacturing, and in agricultural and lubricant applications. Recently, some of these higher oxo alcohols have been used as surface-active agent intermediates. These alcohols, which contain about 75–80% linear isomers, are highly biodegradable but their biodegradability is inversely proportional to the amount of branched isomer present in the final alcohol product. Hence, there is considerable interest in limiting the amount of branched isomer.

SUMMARY OF THE INVENTION

This invention relates to a procedure for the preparation of primary alcohols from predominantly internal olefins having the double bond randomly distributed along the carbon chain wherein the alcohols ($C_{11}$–$C_{14}$) contain more linear isomer (as high as 76%) than those from conventional procedures. (A description of the conventional procedure is given in Examples 4, 5 and 6 wherein the amount of linear isomer in the product ranged from 44% to 55%). In this procedure the internal olefins are contacted with the cobalt source (usually cobalt acetate) and a ligand (usually tri-n-butylphosphine) in the absence of carbon monoxide and hydrogen (synthesis gas) or in the presence of carbon monoxide but without hydrogen. The reaction mixture is heated to the reaction temperature and then the synthesis gas or hydrogen (when carbon monoxide is added initially) is added to the desired pressure. Holding the reaction mixture at around 300° to 500°F for 15 to 30 minutes before hydroformylation has been found to lead to the more desirable alpha structure.

The internal olefins such as dehydrogenated normal paraffins which contain about 10 vol. % internal olefins can be charged alone or in the presence of inert solvents. A hydrogen:carbon monoxide ratio from 1:1 to 3:1 (preferably 2:1) can be used. The cobalt source can be dicobalt octacarbonyl, the cobalt salt of an organic acid (preferably cobalt acetate), cobalt adsorbed on a support or cobalt itself. The ligand can be any tertiary organophosphine (preferably tri-n-butylphosphine). Reaction temperatures from 300°F to 500°F (preferably from 340°F to 400°F), reaction pressures from 1000 to 3500 psig (preferably from 1500 to 2500 psig) and reaction times from 1 to 20 hours (preferably 3 to 10 hours) can be employed.

ANALYSIS OF THE PRIOR ART

Previous work on the preparation of aldehydes and/or alcohols from olefins via the oxo reaction has been extensively reported in the literature. Various catalytic systems and operational procedures have been successfully employed. L. H. Slaugh et al. in U.S. Pat. No. 3,239,569 (1966), developed a modified catalyst system composed of cobalt in complex combination with carbon monoxide and tri-n-butylphosphine. This catalyst system containing strongly basic trialkylphosphine ligands is much more effective in reducing branched isomers in the hydroformylation of 1- and 2-olefins than the conventional oxo catalyst system (HCo(CO)$_4$).

It has also been observed by other researchers that the presence of linear isomers decreased as the chain length of the olefin was increased. Therefore, even though some remarkably high linear/branched product ratios are reported in the literature, the charge is usually a $C_3$ to $C_8$ olefins (usually propylene). The carbon distribution of the internal olefins present in dehydrogenated normal paraffin charge is in the $C_{10}$–$C_{13}$ range, thereby making the predominance of linear products difficult.

A previous experimental procedure for the preparation of alcohols from 1- and 2-hexene is reported in the literature (A. Hershman and J. H. Craddock, I&EC Product Research and Development, Vol. 7, No. 3, p. 227 (1968)). According to this reference the catalyst solution is placed in an autoclave and heated to the desired temperature under a synthesis gas pressure of 100 to 200 psig. The liquid olefin (usually alpha olefins) is then injected and the reactor is pressured to the desired pressure. This procedure differs from the instant invention in that the liquid olefin is charged after reaction temperature is reached. Here the internal olefins, the cobalt source and the ligand are initially charged to the reactor. The reaction mixture is then heated to the desired temperature. Another difference in the instant procedure compared to the literature reference mentioned above is that here the reaction mixture is heated to the desired temperature either without the synthesis gas or with carbon monoxide alone, whereas in the published procedure the synthesis gas (carbon monoxide and hydrogen) is charged to the reactor before heating up the desired temperature.

The marked advantage of the present procedure over a conventional reaction procedure of charging the catalyst solution and internal olefins to the reactor, pressuring the reactor to the desired initial pressure with synthesis gas and heating the mixture to the reaction temperature; is that higher yields of the commercially desired linear products are obtained. The linear/branched product ratios obtained from our novel procedure are comparable to those obtained for hydroformylation reactions starting with alpha olefins in the same carbon number range as shown in Example 7 below.

DESCRIPTION OF PREFERRED EMBODIMENTS

EXAMPLE 1

Cobalt acetate tetrahydrate (4.9 g., 0.02 mols of cobalt) tri-n-butylphosphine (8.0 g., 0.04 mols) and the olefins-paraffin mixture containing about 10 volume percent olefins $C_{10}$–$C_{13}$ (400 g., 0.26 mols of olefins) were added to a 1000 ml stainless steel autoclave and the reactor was flushed with nitrogen and then heated with rocking to the reaction temperature (340°F). The reaction mixture was kept at this temperature for 15 minutes. The reactor was then pressured to 2200 psig with synthesis gas (hydrogen:carbon monoxide molar ratio of 2). The reaction was allowed to continue until no further up-take of the synthesis gas was observed. At the end of this time (140 minutes), the autoclave was cooled, vented and emptied. The crude reaction effluent was decobalted with several successive portions of a 10 percent aqueous acetic acid solution. The decobalted reaction effluent was then vacuum fractionated to remove light materials, unreacted olefins and mixed paraffins. The product alcohols were then taken overhead in 76 mole % selectivity* and contained 63% of the linear isomer. Olefin conversion was calculated as 72 wt. %.

*Selectivity to alcohols, $$\text{mol.\%} = \frac{\text{Mols of Alcohol Produced} \times 100}{\text{Mols of Olefin Reacted}}$$

EXAMPLE 2

Cobalt acetate tetrahydrate (4.9 g., 0.02 mols of cobalt), tri-n-butylphosphine (8.0 g., 0.04 mols) and the olefin-paraffin mixture containing about 10 volume percent olefins $C_{10}$–$C_{13}$ (400 g., 0.26 mols of olefins) were added to the 1000 ml stainless steel autoclave, and the reactor was flushed with nitrogen and then heated with rocking to the reaction temperature (340°F). When the reaction temperature was reached, the reaction mixture was kept at this temperature for 15 minutes. After this 15 minute holding period, the reactor was pressured to 2200 psig with synthesis gas (hydrogen:carbon monoxide molar ratio of 2). The reaction was allowed to continue until no further up-take of the synthesis gas was observed. At the end of this time (185 minutes), the autoclave was cooled, vented and emptied. The crude reaction effluent was decobalted with several successive portions of a 10 percent aqueous acetic acid solution. The decobalted reaction effluent was then vacuum fractionated to remove light materials, unreacted olefins and mixed paraffins. The product alcohols were then taken overhead in 60 mol % selectivity and contained 68% of the linear isomer. Olefin conversion was calculated as 63 wt. %.

EXAMPLE 3

Cobalt acetate tetrahydrate (4.9 g., 0.02 mols of cobalt), tri-n-butylphosphine (8.0 g., 0.04 mols) and the olefin-paraffin mixture containing about 10 volume percent olefins $C_{10}$–$C_{13}$ (400 g., 0.26 mols of olefin) were added to the 1000 ml stainless steel autoclave and the reactor flushed with nitrogen and then heated with rocking to the reactor temperature (340°F). When the reaction temperature was reached, the reaction mixture was kept at this temperature for 15 minutes. After this 15 minutes holding period, the reactor was pressured to 2200 psig with synthesis gas (hydrogen:carbon monoxide molar ratio of 2). The reaction was allowed to continue until no further up-take of the synthesis gas was observed. At the end of this time (287 minutes), the autoclave was cooled, vented and emptied. The crude reaction effluent was vacuum fractionated to remove light materials and unreacted olefins and mixed paraffins. The bottoms from the distillation, which contained the product alcohols, were decobalted with several successive portions of an aqueous 10 percent acetic acid solution. The product alcohols were collected in 65 mol % selectivity and contained 76% of the linear isomer. Olefin conversion was calculated as 70 wt. %.

COMPARATIVE EXAMPLES 4-7

The following examples show results obtained using conventional procedures or in the case of Example 7, alpha olefins as charge stock.

EXAMPLE 4

Cobalt acetate tetrahydrate (4.9 g., 0.02 mols of cobalt), tri-n-butylphosphine (8.0 g., 0.04 mols) and the olefin-paraffin mixture containing about 10 volume percent olefins $C_{10}$–$C_{13}$ (400 g., 0.26 mols of olefins) were added to the 1000 ml stainless steel autoclave and the reactor was flushed with synthesis gas (hydrogen:carbon monoxide molar ratio of 2), pressured to 1700 psig and heated to the reaction temperature (340°F). The reaction was allowed to continue until no further up-take of the synthesis gas was observed. At the end of this time (73 minutes), the autoclave was cooled, vented and emptied. The crude reaction effluent was stirred and refluxed with several successive portions of an aqueous 10 percent acetic acid solution to decompose the cobalt carbonyls and remove the cobalt from the organic medium as a water soluble salt. The decobalted reaction effluent was then vacuum fractionated to remove light materials, unreacted olefins and mixed paraffins. The product alcohols were then taken overhead in 73 mol % selectivity and contained 52% of the linear isomer. Olefin conversion was calculated as 72 wt. %.

EXAMPLE 5

Cobalt acetate tetrahydrate (4.9 g., 0.02 mols of cobalt), tri-n-butylphosphine (8.0., 0.04 mols), stearic acid (11.4 g., 0.040 mols) and the olefin-paraffin mixture containing about 10 volume percent olefins $C_{10}$–$C_{13}$ (400 g., 0.26 mols of olefins) were added to the 1000 ml stainless steel autoclave and the reactor was flushed with synthesis gas (hydrogen:carbon monoxide molar ratio of 2), pressured to 1700 psig and heated to the reaction temperature (340°F). The reaction was allowed to continued until no further uptake of the synthesis gas was observed. At the end of this time (60 minutes), the autoclave was cooled, vented and emptied. The crude reaction effluent was decobalted with several successive portions of an aqueous 10 percent acetic acid solution. The decobalted reaction effluent was then vacuum fractionated to remove light materials, unreacted olefins and mixed paraffins. The product alcohols were then taken overhead in 72 mol % selectivity and contained 47% of the linear isomer. Olefin conversion was calculated as 84 wt. %.

A second run conducted under the same reaction conditions and charge stock quantities as above yielded product alcohols in 83 mol. % selectivity. The product alcohols contained 55% of the linear isomer. Olefin conversion was calculated as 85 wt. %.

EXAMPLE 6

Cobalt stearate (2.3 g., 0.004 mols of cobalt), tri-n-butylphosphine (0.8 g., 0.004 mols) and the olefin-paraffin mixture containing about 10 volume percent olefins $C_{10}-C_{13}$ (400 g., 0.26 mols of the olefin) were added to the 1000 mol stainless steel autoclave and the reactor was flushed with synthesis gas (hydrogen:carbon monoxide ratio of 2), pressured to 1700 psig and heated to the reactor temperature (340°F). The reaction was allowed to continue until no further up-take of the synthesis gas observed. At the end of this time (45 minutes), the autoclave was cooled, vented and emptied. The crude reaction was decobalted with several successive portions of an aqueous 10 percent acetic acid solution. The decobalted reaction effluent was then vacuum fractionated to remove light materials, unreacted olefins and mixed paraffins. The product alcohols were then taken over head in 32 mol % selectivity and contained 44% of the linear isomer. Olefin conversion was calculated as 85 wt. %.

EXAMPLE 7

Dicobalt octacarbonyl (5.3 g., 0.031 mols of cobalt) tri-n-butylphosphine (6.2 g., 0.031 mols), stearic acid (17.8 g., 0.063 mols) and $C_{11}-C_{14}$ alpha olefin (172.8 g., 1.0 mols) were added to the 1000 ml stainless steel autoclave and the reactor was purged with synthesis gas ($H_2$:CO mol ratio, 2:1) and then pressured to 1300 psig with the synthesis gas ($H_2$:CO mol ratio, 2:1). The reaction mixture was heated with rocking to the reaction temperature (383°F). The reaction was allowed to continue until no further up-take of the synthesis gas was observed. At the end of this time (180 minutes), the autoclave was cooled, vented and emptied. The crude reaction effluent was decobalted with several successive portions of a 10 percent aqueous acetic acid solution. The decobalted reaction effluent was then vacuum fractionated to remove light materials. The product alcohols were then taken overhead in 86 mol % selectivity and contained 74% of the linear isomer. Olefin conversion was calculated as 82 wt. %.

EXAMPLE 8

Cobalt acetate tetrahydrate (4.9 g., 0.02 mols of cobalt), tri-n-butylphosphine (8.0 g., 0.04 mols) and the olefin-paraffin mixture containing about 10 volume percent olefins (400 g., 0.26 mols of olefins) were added to a 1000 ml. stainless steel autoclave and the reactor was flushed with nitrogen and then heated with rocking to the reaction temperature (340°F). The reaction mixture was kept at this temperature for 30 minutes. The reactor was then pressured to 2200 psig with synthesis gas (hydrogen:carbon monoxide molar ratio of 2). The reaction was allowed to continue until no further up-take of the synthesis gas was observed. At the end of this time, the autoclave was cooled, vented and emptied. The crude reaction effluent was decobalted with several successive portions of a 10 percent aqueous acetic acid solution. The decobalted reaction effluent was then vacuum fractionated to remove light materials, unreacted olefins and mixed paraffins. The product alcohols were then taken overhead in 75 mol % selectivity and contained 70% of the linear isomer. Olefin conversion was calculated as 70 wt. %.

The important fact to observe in comparing the data of Example 1–3 with those of Examples 4–6 is that the former gave as high as 76% linear isomers while the conventional procedure of Examples 4–6 gave only from 44 to 55%. These results compared favorably with that of Example 7 where starting with an alpha olefin charge the product alcohols contained 74% of the linear isomer. Thus the results of Examples 1–3 point out the unobvious nature of the present invention.

Similarly hydroformylated with good results were $C_4-C_7$, $C_7-C_9$, and $C_{14}-C_{17}$ olefinic fractions so that the process of the invention can be said to apply generally to predominantly internal olefins having from 4 to 17 carbon atoms per molecule.

We claim:

1. A two step process for the conversion of a feed charge consisting of predominantly internal olefins having from 4 to 17 carbon atoms per molecule to the corresponding linear alcohols having one more carbon atom to the molecule than said olefins which comprises heating said charge with a cobalt salt of an organic acid and a ligand consisting of a tertiary organophosphine at a reaction temperature of from about 300°F to about 500°F in the absence of carbon monoxide and hydrogen or in the presence of carbon monoxide but without hydrogen thereby isomerizing said olefins to their alpha structure; maintaining the reaction mixture at said temperature for about 15 to 30 minutes; then hydroformylating said alpha olefins by contacting said reaction mixture containing said alpha olefins with synthesis gas under a pressure of from about 1000 to 3500 psig for a reaction time of from about 1 to 20 hours and recovering predominantly linear primary alcohols.

2. The process of claim 1 wherein the isomerizing reaction pressure ranges from 1500 to 2500 psig.

3. The process of claim 1 wherein hydroformylation reaction time ranges from 3 to 10 hours.

4. The process of claim 1 wherein said olefins are present in a charge of dehydrogenated normal paraffins.

5. The process of claim 1 wherein said cobalt salt of an organic acid is cobalt acetate.

6. The process of claim 1 wherein said ligand is tri-n-butylphosphine.

7. The process of claim 1 wherein isomerizing is carried out at 340°F to 400°F.

* * * * *